United States Patent [19]
Rink et al.

[11] Patent Number: 5,814,600
[45] Date of Patent: Sep. 29, 1998

[54] METHOD AND COMPOSITION FOR TREATMENT OF INSULIN REQUIRING MAMMALS

[75] Inventors: Timothy J. Rink, La Jolla; Andrew A. Young, Alpine, both of Calif.

[73] Assignee: Amylin Pharmaceuticals Inc., San Diego, Calif.

[21] Appl. No.: 259,762

[22] Filed: Jun. 13, 1994

Related U.S. Application Data

[63] Continuation-in-part of Ser. No. 127,705, Sep. 27, 1993, abandoned, which is a continuation of Ser. No. 704,995, May 24, 1991, abandoned.

[51] Int. Cl.$^6$ .................................................. A61K 38/28
[52] U.S. Cl. .................................. 514/4; 514/12; 514/21; 514/3
[58] Field of Search ................................ 514/3, 4, 12, 21

[56] References Cited

U.S. PATENT DOCUMENTS

| | | | |
|---|---|---|---|
| 5,124,314 | 6/1992 | Cooper | 514/4 |
| 5,234,906 | 8/1993 | Young et al. | 514/12 |
| 5,508,260 | 4/1996 | Beaumont et al. | 514/4 |
| 5,527,771 | 6/1996 | Beaumont et al. | 514/12 |
| 5,686,411 | 11/1997 | Gaeta et al. | 514/12 |

FOREIGN PATENT DOCUMENTS 0309100  3/1989  European Pat. Off. .

*Primary Examiner*—Chhaya D. Sayala

[57] ABSTRACT

Method and compositions for treating a mammal by administering to that mammal an insulin (having the in vitro activity of stimulating glucose incorporation into glycogen in rat soleus muscle) and an amylin (having the in vitro activity of suppressing glucose incorporation into glycogen in rat soleus muscle) using specific molar ratios of an insulin to an amylin.

32 Claims, 11 Drawing Sheets

INTER-PEPTIDE (HUMAN)

```
AMYLIN   K C N T A T C A T Q R L A N F L V H S S N N F G A I L S S T N V G S N T Y - - - - NH2
CGRP-1   A - D - - - V - H - - - - - - - - - - - - - - G L - S R - G G V V K N N F V P - - - K A F - NH2
CGRP-2   A - - - - - V - H - - - - - - - - - - - - - - G L - S R - G G N V K S N F V P - - - K A F - NH2
```

INTER-SPECIES (AMYLINS)

```
HUMAN      K C N T A T C A T Q R L A N F L V H S S N N F G A I L S S T N V G S N T Y - NH2
BABOON     - - - - - - - - - - - - - - - - - - - - - - - - - - - - - - - - - - - - - NH2
MONKEY     - - - - - - - - - - - - - - - - - - - - - - - - - - - - - - - - - - - D - NH2
CAT        - - - - - - - - - - - - - - - - - R - - - - - - - - T - - - - - - - - - - - NH2
DOG        - - - - - - - - - - - - - - - - - I R - - - - - - - L - - - - - P - - - - - NH2
RAT        - - - - - - - - - - - - - - - - - R T - - - - - - - L - - - - - P - - - - - NH2
MOUSE      - - - - - - - - - - - - - - - - - R - - - - - - - - L - - - P V - P P - - - NH2
HAMSTER    - - - - - - - - - - - - - - - - - R - - - - - - - - L - - - P V - P P - - - NH2
GUINEA PIG - - - - - - - - - - - - - - - - - - - - N - - - - - L - - - P V - P - - - - NH2
           - - - - - - - - - - - - - - - - - R - - - H - - - - L - - - A - L P - D - - NH2
DEGU       - - - - - - - - - - - - - - - - - R - - - H - - - - L - - - A - P P - K - - NH2
```

Fig. 1

METHOD AND COMPOSITION FOR TREATMENT OF INSULIN REQUIRING MAMMALS

RELATED APPLICATIONS

This application is a continuation-in-part of application Ser. No. 08/127,705 filed Sep. 27, 1993 which is a continuation of application Ser. No. 07/704,995 filed May 24, 1991 both abandoned.

FIELD OF THE INVENTION

This invention relates to therapeutic amounts or dosages of an amylin and to therapeutic combinations of insulin and amylin and their use for treatment of insulin deficient mammals, such as diabetic humans.

BACKGROUND OF THE INVENTION

Human diabetics are deficient in insulin secretion, and in some cases lack insulin. Insulin is one of several hormones which play a role in regulation of blood glucose levels. Simplistically, there are two main stores of glucose in a mammal—the liver and skeletal muscle, where glucose is stored in the form of glycogen. Muscle glycogen is used as a glucose source for the muscle, whereas liver glycogen is used as a glucose source for all tissues, including blood. It is the interplay of certain hormones in regulation of glycogen accumulation and breakdown that is critical in the invention described below.

Insulin regulates glucose uptake by muscle tissue for storage of the glucose as muscle glycogen. Insulin also prevents hyperglycemia, that is, the unacceptable accumulation of high levels of glucose in the blood, and suppresses conversion of liver glycogen to glucose, and subsequent secretion of that glucose into the blood. In the presence of excess insulin, blood glucose accumulates in muscle tissue as glycogen, liver glucose output is suppressed, and the level of blood glucose falls, to create a condition termed hypoglycemia.

Another hormone, glucagon, increases blood glucose levels by stimulating liver glycogen breakdown to glucose, and subsequent secretion of that glucose. This liver glycogen is used to maintain blood glucose levels, and glucagon may be considered an insulin counterregulatory hormone.

Amylin is another hormone which has been discovered to be concerned in regulation of blood glucose levels. It reverses insulin-mediated suppression of liver glucose output in rats. Molina et al., 39 *Diabetes* 260, 1990, and Koopmans et al., 39 *Diabetes* 101A, 1990.

European Patent Application No. 88307927.9 describes the treatment of diabetes mellitus or hypoglycemia with amylin and CGRP, an amylin agonist, alone or in combination with insulin, preferably at a ratio of between 100:1 to 0.1:1 insulin to amylin or CGRP. The applicant reports that the major problem with insulin treatment of diabetes is hypoglycemia and that co-administration of insulin and amylin or CGRP may avoid this side effect. The application states that amylin exerts a powerful modulating effect on insulin-induced storage of glucose as glycogen, and that amylin may act to modulate and reduce the hypoglycemic effects of insulin by reducing release of insulin in relation to a given glucose stimulus, and by reducing the rate of storage of glucose as muscle glycogen. That is, amylin should reduce insulin-sensitivity and cushion the hypoglycemic effects of insulin.

SUMMARY OF THE INVENTION

Applicants' invention is concerned with discovery of a further surprising relationship between amylin and insulin. It also relates to the unexpected discovery of particularly effective dosages of an amylin, and optimum ratios of insulin and amylin used for treatment of mammals suffering from diabetes, or other insulin deficient mammals. Applicant has discovered that it is preferable to provide an amylin at a dosage of at least about 0.2 micrograms per kilogram per day, preferably at least about 0.4 micrograms per kilogram per day, and more preferably at least about 0.5 micrograms per kilogram per day. Applicants have also discovered that it is preferable to maintain a ratio of amylin and insulin within a mammal in a relatively narrow range or ranges in order that both the amylin and insulin will have optimal effects, and may prevent the damaging side effects of either excess amylin or insulin alone.

In view of amylin's antagonism of muscle response to insulin, others have postulated that the effects of amylin and insulin would simply cancel each other out in vivo. However, applicants discovered that not only is this not the case, but that amylin suppression of the insulin response of a patient is increased as the hormonal concentrations increase above a certain value. Thus, when the hormones are provided in a fixed ratio, the effects of each hormone may be moderated, and the damaging effect of either hormone alone at high concentration may be prevented.

Applicants discovered that provision of amylin and insulin at a constant molar ratio results in a bell-shaped dose response relationship between hormone levels and glucose disposal in skeletal muscle, but not in other tissue. This discovery indicates that amylin and insulin act independently of one another, and are non-competitive functional antagonists for certain key metabolic responses, including glucose uptake into skeletal muscle glycogen and hepatic glucose output. Applicants propose in this invention that patients suffering from diabetes may be treated in a manner which maintains the insulin and amylin within the patient at relatively constant proportions which may be similar to those present in normal mammals under physiologic conditions. This is advantageous because, at normal physiologic insulin concentration, the response of the body to insulin is not much altered in the presence of amylin, but at high insulin levels the response is considerably lower than maximum in the presence of amylin. Thus, insulin mediated side-effects are suppressed by amylin at high insulin concentrations. Administration of insulin and amylin in a given proportion or the provision of at least about 0.2 micrograms per kilogram per day, preferably at least about 0.4 micrograms per kilogram per day, and more preferably at least about 0.5 micrograms per kilogram per day amylin, may reduce the risk of hypoglycemia that would otherwise follow, for example, from the introduction of excessive levels of insulin. Still more preferably, an amylin is administered at a dosage of from about 0.2 micrograms per kilogram per day to about 5 micrograms per kilogram per day, about 0.4 micrograms per kilogram per day to about 2.0 micrograms per kilogram per day. In the regime proposed, the patient may be protected from an overdose of insulin since amylin dampens potential oscillations of plasma-glucose level caused by poor insulin regulation. Without being bound to any theory, applicants believe that the coadministered amylin operates by restoring hepatic glycogen stores so that, in the presence of insulin, such glycogen is mobilized by glucagon.

In light of available data, still others have viewed amylin therapy with further skepticism, arguing that amylin effects can be seen only with large, "industrial strength" doses. Importantly, as described in Example 3 below, applicants have now shown that administration of amylin agonist doses as low as 90 micrograms per day significantly helped control blood glucose levels in diabetic patients by reducing average blood glucose after a meal. The results were statistically significant and are medically highly relevant in view of the blood glucose control problems that plague diabetics throughout their lives and, more specifically, for example, because of the abnormally high post-meal glucose levels typical of juvenile-onset diabetes which are understood to be a continuing factor in the onset of long-term medical complications, including blindness, kidney failure, and nerve damage.

One aim of coadministration of amylin and insulin in diabetes is to restore, as far as practicable, the most effective ratio of these hormones. Thus, the dose of each will reflect their respective deficit due to beta cell loss, and will be related approximately in the ratio of amylin to insulin normally co-secreted by a pancreatic beta cell. Applicants have discovered that a molar ratio of between about 1.5% and about 50% amylin to insulin, preferably between about 3% and about 40% amylin to insulin is indicated, i.e., an amylin to insulin ratio of about 1:67 to about 1:1, or between about 1:35 to about 1:2.5. This may vary for different patients and the approximate ratio will be determined by (1) monitoring residual amylin and insulin levels by plasma immunoassay, and (2) by normal practice clinical monitoring of plasma glucose and clinical state.

It is desirable to provide relatively constant amylin:insulin ratios, particularly when insulin levels are likely to be changing. It is not necessarily the case, however, that a depot form of amylin, to match, say, ultralente insulin will be required (although it is provided for by the instant invention). Ultralente provides a rather steady basal insulin level, not predicted to elicit hypoglycemic episodes. The main need is for effective levels of amylin to accompany and track insulin levels following administration of faster acting forms of insulin that lead to rapidly changing plasma levels.

Thus, amylin should be formulated to provide a pattern of plasma concentrations which matches, within a factor of about 2.5-fold, in time-to-peak and half-time for disappearance, that of the soluble or rapid-acting insulin being administered to a patient. In this way, amylin may be most moderating of insulin action when insulin is the higher concentration range, and will leave insulin action essentially intact as plasma levels due to soluble insulin decline. The amylin administered will not significantly impact the ability of the ultralente contribution of basal insulin to limit upswings in plasma glucose.

In summary, the preferred formulation for amylin is one which provides amylin/insulin concentrations ratios within about 33% to about 300% of those in normal subjects for 4 hours following administration of the patient's most rapid acting insulin dosage, and matches, within a factor of about 3-fold, the time-to-peak and the time course of decline of plasma insulin levels.

Thus, in a first aspect, the invention features a method for treating a mammal by administering to that mammal an insulin (having the in vitro activity of stimulating glucose incorporation into glycogen in rat soleus muscle) and an amylin (having the in vitro activity of suppressing glucose incorporation into glycogen in rat soleus muscle) at a molar ratio of between about 1:1 and about 67:1, preferably between about 7:1 and about 67:1, and more preferably between about 1:1 and about 40:1.

By "an insulin" is meant any insulin of natural or synthetic origin, and functional peptide fragments and conservative variants Of an insulin which may be used in conventional treatment of diabetes mellitus. It is important in this invention, and it is clear to those of ordinary skill in this art, that the insulin polypeptide fragment need only have an insulin activity characterized by the in vitro activity of stimulating glucose incorporation into glycogen in rat soleus muscle, as described in detail below. Thus, the insulin may be produced in any standard manner including, but not limited to, extraction of bovine and porcine pancreatic insulin, expression of the insulin from recombinant DNA, and in vitro polypeptide synthesis of fragments of insulin. The insulin may also be provided in a fast-acting or semilente form.

By conservative variant is meant an insulin polypeptide which has substantial (at least 90% of a contiguous ten amino acid sequence) amino acid sequence identity with a naturally occurring insulin, or one used in conventional treatment of diabetes mellitus, but which has one or more amino acids in such a sequence substituted in a conservative manner, such that the biological activity of the insulin remains substantially intact. Examples of such a conservative substitution includes substituting positively charged amino acids for other positively charged amino acids, negatively charged amino acids for other negatively charged amino acids, and simple amino acids, such as glycine, for other such amino acids, such as valine. Useful insulins for this invention can be readily determined by testing a chosen insulin for the desired activity in the in vitro test described below, or any equivalent in vitro or in vivo test.

By "an amylin" is meant any agonist molecule which includes a functional peptide fragment of a naturally occurring amylin, carboxy-deamidated amylin or calcitonin gene related peptide (CGRP) which includes at least five amino acid residues and has the in vitro activity described above. In addition, it is preferred that such an amylin perform in vivo a therapeutic function of the complete amylin or CGRP peptide. The term also includes conservative variants and functional peptide fragments of such peptides. Examples of such amylins are provided in FIG. 1 where sequence homologies among amylins in humans and other species are shown (using a standard one letter amino acid code). Preferably, the amylin has a Kd of less than 60 pMolar in a receptor assay, and an $EC_{50}$ of less than 1 nMolar in a rat soleus assay (FIG. 7, see below). More preferably, the amylin is one of the compounds described in Gaeta et al., U.S. patent application Ser. No. 07/794,266, filed Nov. 19, 1991, U.S. Pat. No. 5,686,411 which application is hereby incorporated by this reference. Most preferably, the amylin is $^{25,28,29}$Pro-human-amylin (also referred to as "triproamylin" or as "AC-0137").

Those of ordinary skill in this art will recognize that the above terms "insulin" and "amylin" can be read broadly to include any polypeptide or other chemical class having the above described desired biological activity, in vitro or in vivo, which stimulates or suppresses, respectively, glucose incorporation into glycogen in any of many test systems, including, rat soleus muscle. In addition, such persons recognize that the polypeptide may be provided in a form which does not significantly affect the desired biological activity of the polypeptide. For example, as described in European Patent Application No. 88307927.9, supra, the amylin may be prepared in a soluble form.

In preferred embodiments, the method includes the step of identifying a mammal having a need for, or a reduced ability to produce, insulin compared to a normal mammal, prior to administering the amylin or insulin and amylin to the mammal. Most preferably, the mammal is a human, e.g., suffering from diabetes mellitus.

In other preferred embodiments, the insulin and amylin are provided in a molar ratio between about 1:1 to about 67:1, or between about 7:1 to about 67:1, or between about 1:1 and about 40:1, or between about 2.5:1 and about 35:1 or about 5:1 and about 25:1, or between about 5:1 to about 10:1. In still other preferred embodiments, an amylin is provided at a dosage of at least about 0.2 micrograms per kilogram per day, preferably at least about 0.4 micrograms per kilogram per day, and more preferably, at least about 0.5 micrograms per kilogram per day.

In a second aspect, the invention features a method for treating a mammal by first determining the level of an insulin and an amylin in the mammal, and then administering an amount of an insulin and an amylin which will provide a molar ratio of insulin and amylin in the serum of the animal between about 1:1 and about 67:1, between about 7:1 and about 67:1, between about 1:1 and about 40:1, between about 2.5:1 and about 35:1, between about 5:1 and about 25:1 and between about 4:1 or 5:1 to about 10:1.

The level of insulin and amylin in the mammal may be determined by any desired means, many examples of which exist in the published literature. In addition, amylin activity can be assayed as described by Cooper and Young, U.S. Ser. No. 07/666,512, entitled "Amylin Activity Assays", filed Mar. 8, 1991, now abandoned assigned to the same assignee as the present application, and hereby incorporated by reference herein.

In a third aspect, the invention features a composition including an insulin and an amylin in a molar ratio of between about 1:1 and about 40:1, between about 2.5:1 and about 35:1, between about 5:1 and about 25:1 and between about 4:1 or 5:1 to about 10:1. Preferably, this composition is provided in a form which allows delayed release of both the insulin and amylin in a constant molar ratio, or in a form suitable for parenteral administration.

In a related aspect, the invention features a method for treating a mammal by administering to that mammal a composition containing an insulin and an amylin at a suitable molar ratio, such that the amount of amylin in the composition will result in circulating plasma levels of amylin that are about 3 to about 6% preferably about 4 to about 7%, that of insulin upon administration of the composition to the patient. However, such levels of amylin may be as high as about 14% to about 23%.

One of the main advantages of the present invention is that insulin-requiring diabetics will be less concerned about insulin overdose so long as the correct ratio of amylin is also provided with that insulin. At present, in order to avoid the acutely unpleasant effects of hypoglycemia, patients characteristically tend to hold back on their insulin therapy, preferring to live with higher levels of plasma glucose which do not present any immediately discernible pathologies. However, the resulting chronic hyperglycemia leads to vascular defects, insulin resistance, and abnormal carbohydrate metabolism. With the present invention, such diabetics need no longer live in this chronic state of hyperglycemia. Thus, the optimum amylin/insulin combination of this invention aids in overcoming long-term complications normally associated with insulin therapy.

The amylin and amylin/insulin formulations of this invention provides patients who inject their own insulin with an improved formulation that may reduce the occurrence of low plasma glucose levels. These formulations impede glucose disposal into skeletal muscle when plasma glucose levels are depressed, stimulate hepatic glycogen synthesis to ensure an effective counterregulatory response to hypoglycemia, and permit essentially normal insulin control of hyperglycemia.

The amylin and the blended insulin-amylin formulations place a limit on the rate of glucose disposal into skeletal muscle, which may decrease the risk of hypoglycemia associated with aggressive hormone therapy. Additionally, the amylin will restore fatty acid synthesis from lactate and provide the patients a more normal body fat distribution.

Other advantages of this invention to diabetics include lower average plasma glucose levels; reduced long term complications; relaxation of monitoring needs; less need for rigorous definition of insulin dosage; greater freedom to vary size and timing of hormone therapy, and the extent and timing of any rigorous activity; and a better sense of well being.

As with insulin alone, the above insulin/amylin formulations can be tailored by standard techniques to the specific physiological requirements of each patient.

It will be recognized by those in the art that the dosages of an amylin described herein can be given in divided amounts, most typically before meals, and/or in a slow or sustained release (e.g., lente or ultralente) forms. Preferably, lower dosages may be given in rapid acting (e.g., soluble or solution) form, and higher dosages may be given in slow-or sustained-release forms (e.g., designed to release an amylin, such as tripro-amylin, over a period of 12, 24 or 48 hours).

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1 is a representation, using standard single letter nomenclature to represent amino acids, of the amino acid sequence of amylin and related polypeptides;

Figure 5:
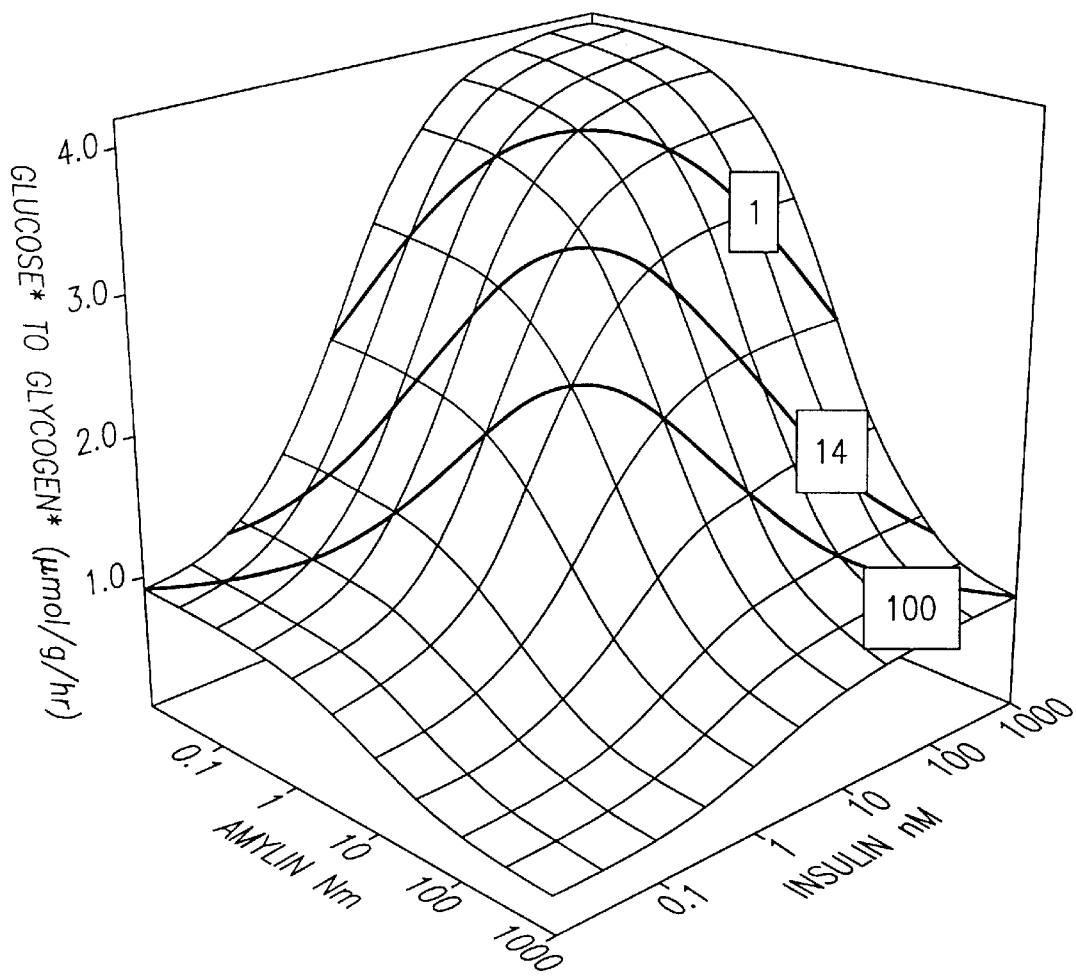

FIG. 5 is a graphical representation showing an insulin/ amylin dose response surface, the lines labelled 1, 14, and 100 representing the predicted responses for insulin/amylin mixtures where amylin is at 1%, 14% and 100% of the molar concentration of insulin, respectively.

Figure 6:
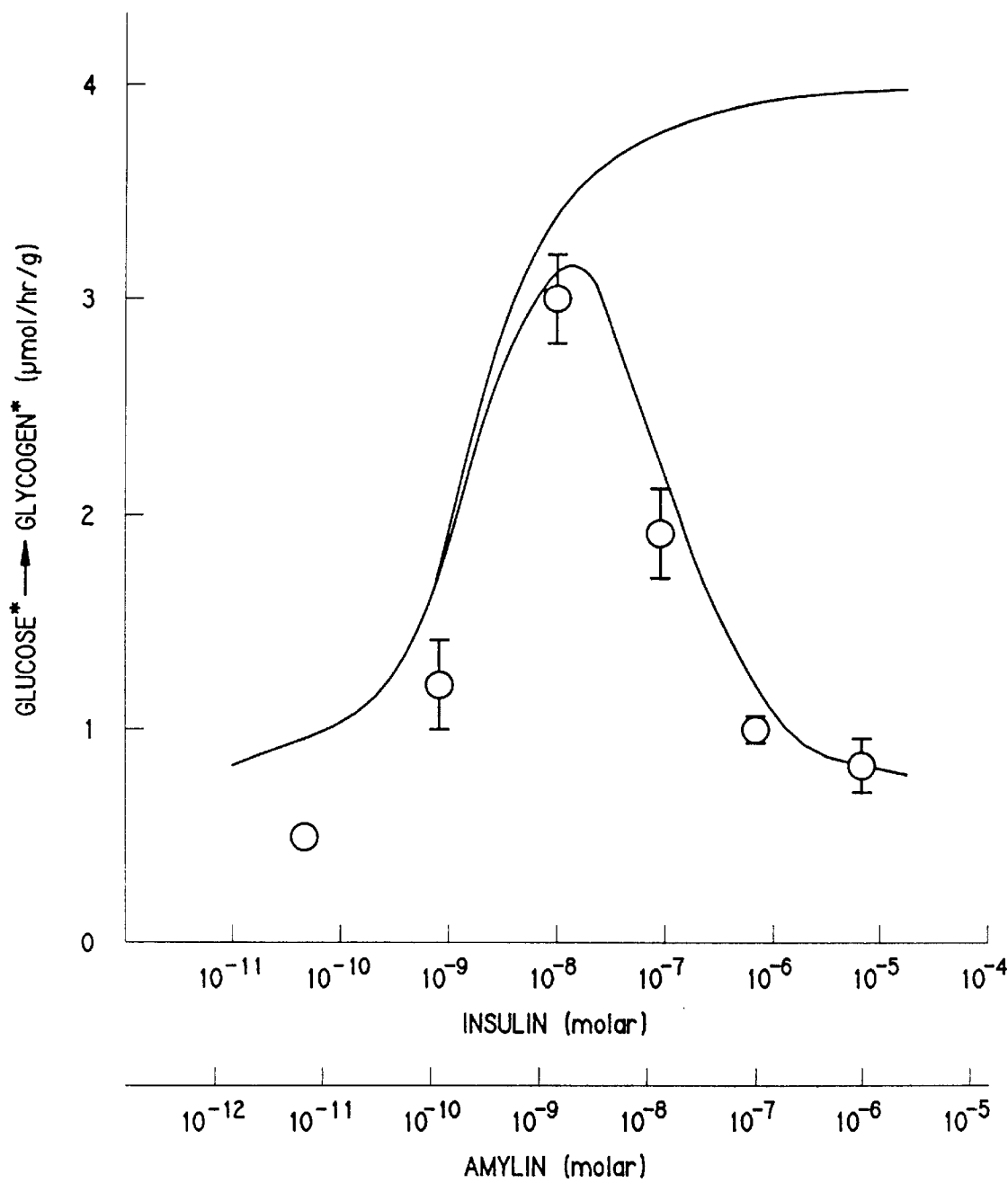
Figure 7:
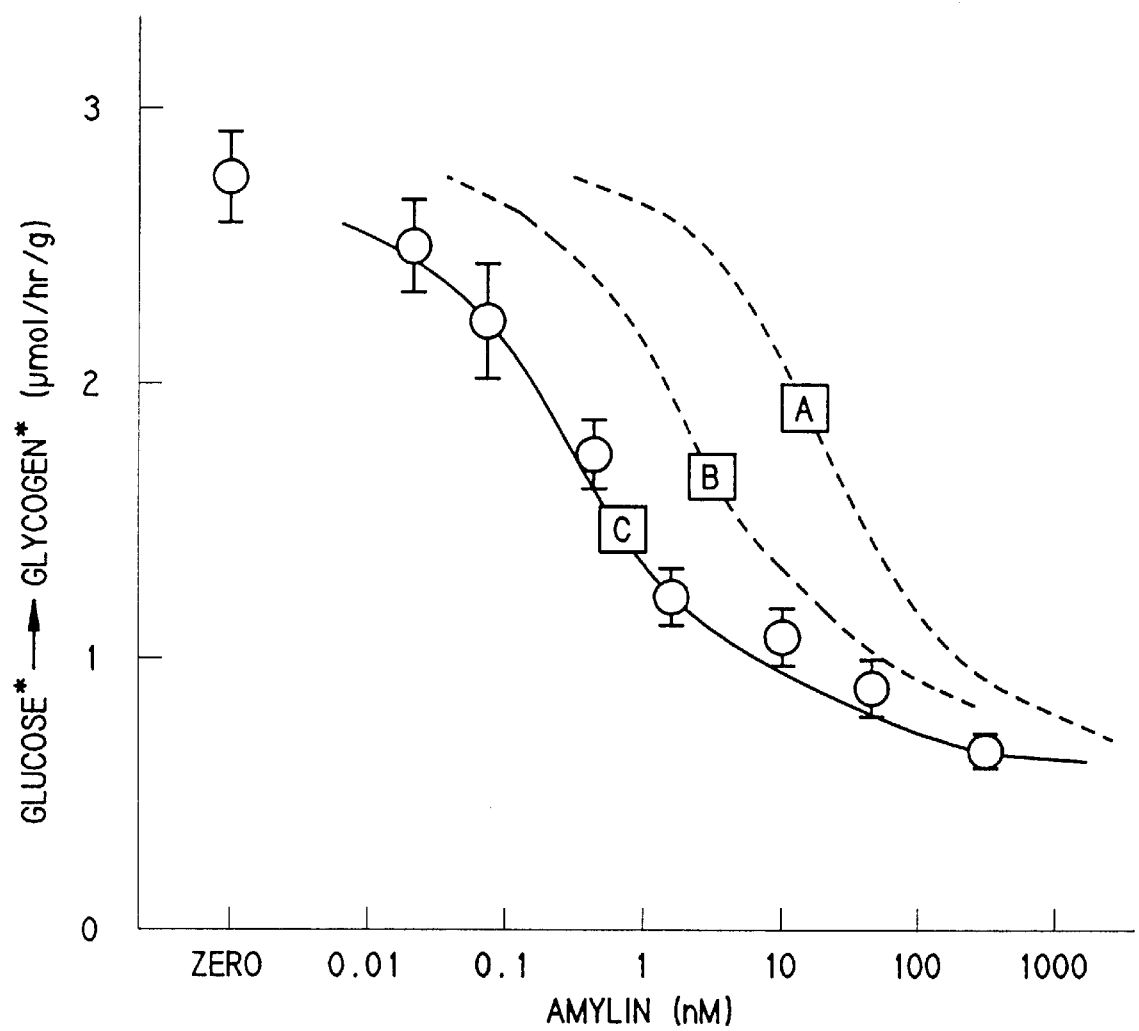
Figure 8:
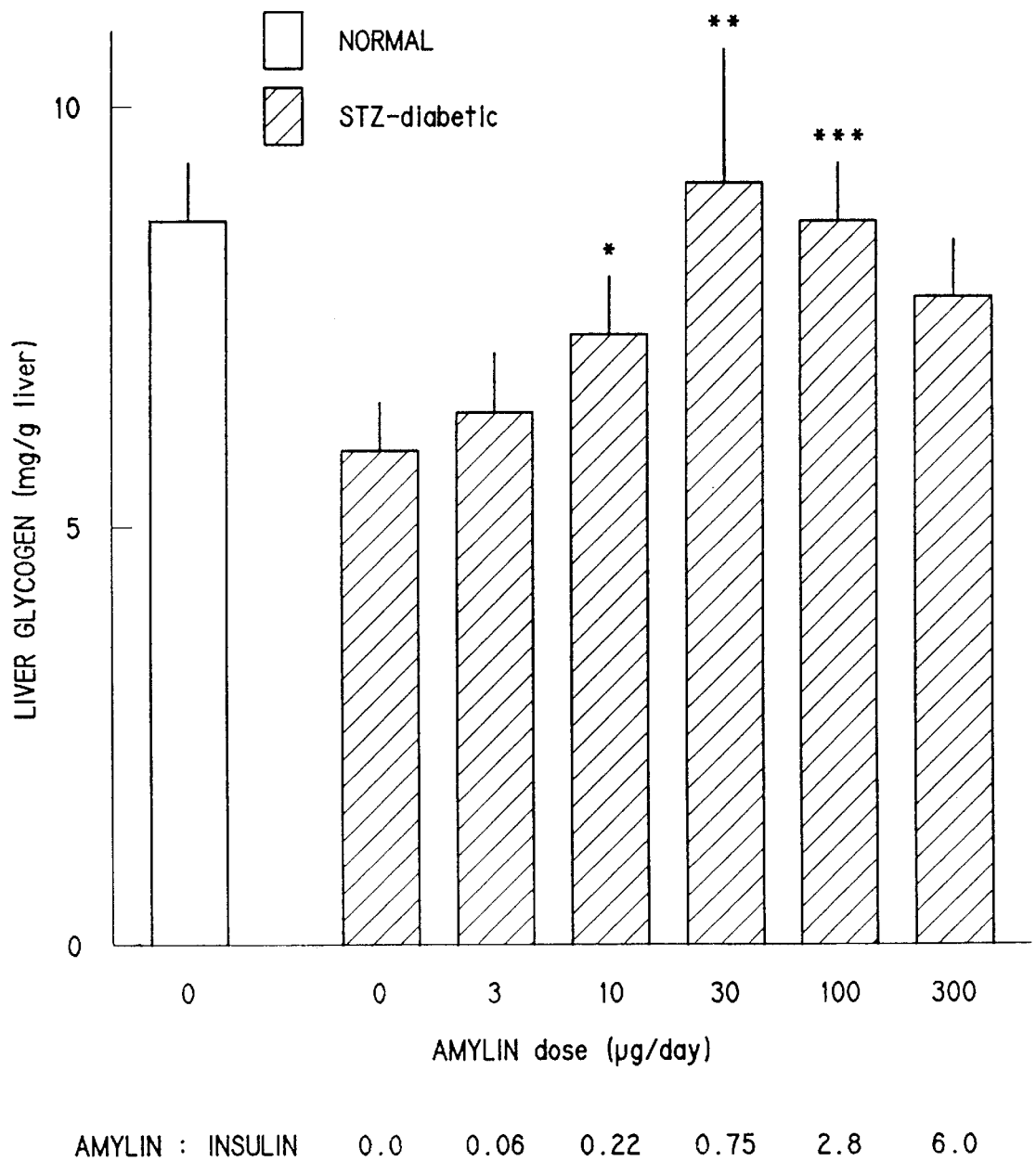

FIG. 6 is a graphical representation showing response to increasing insulin and amylin concentration in a fixed ratio of 7 to 1; the upper line shows the sigmoid dose response for insulin alone;

FIG. 7 is a graphical representation showing amylin dose response curves utilizing three different methods for measuring experimental amylin concentrations; and FIG. 8 is a graphical representation of liver glycogen levels in rats, showing the effect of insulin and insulin/ amylin combinations in restoring glycogen levels in streptozotoan-treated diabetic rats.

Figure 9:
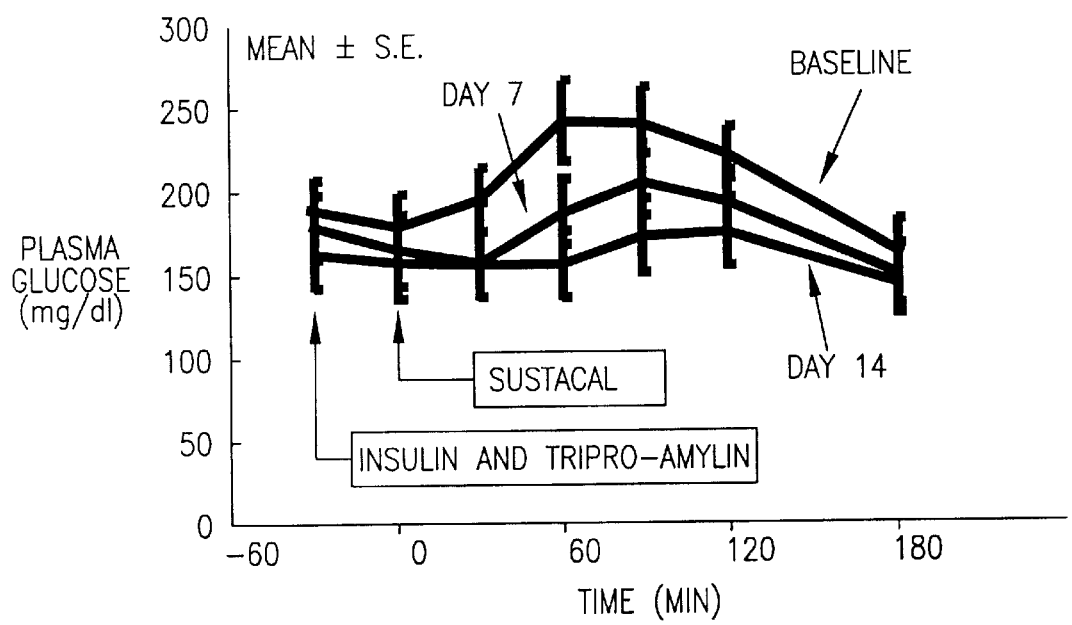
Figure 9A:
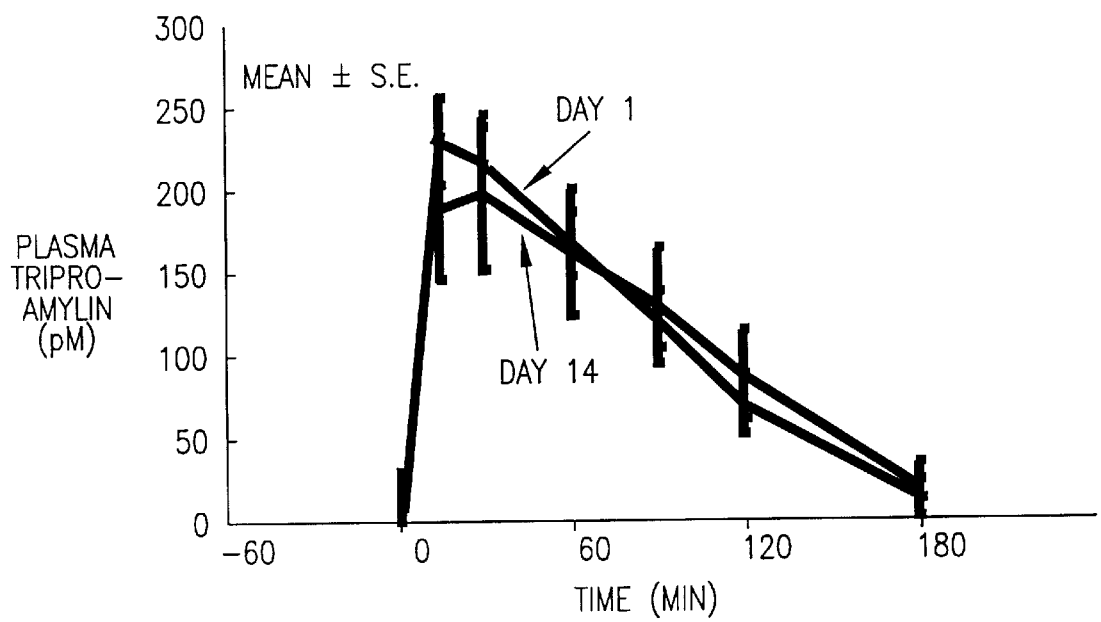

FIG. 9 shows the reduction in post-meal plasma glucose levels, or "glucose smoothing" effect, produced in diabetics administered 30 micrograms of tripro-amylin three times per day over 14 days.

Figure 10:
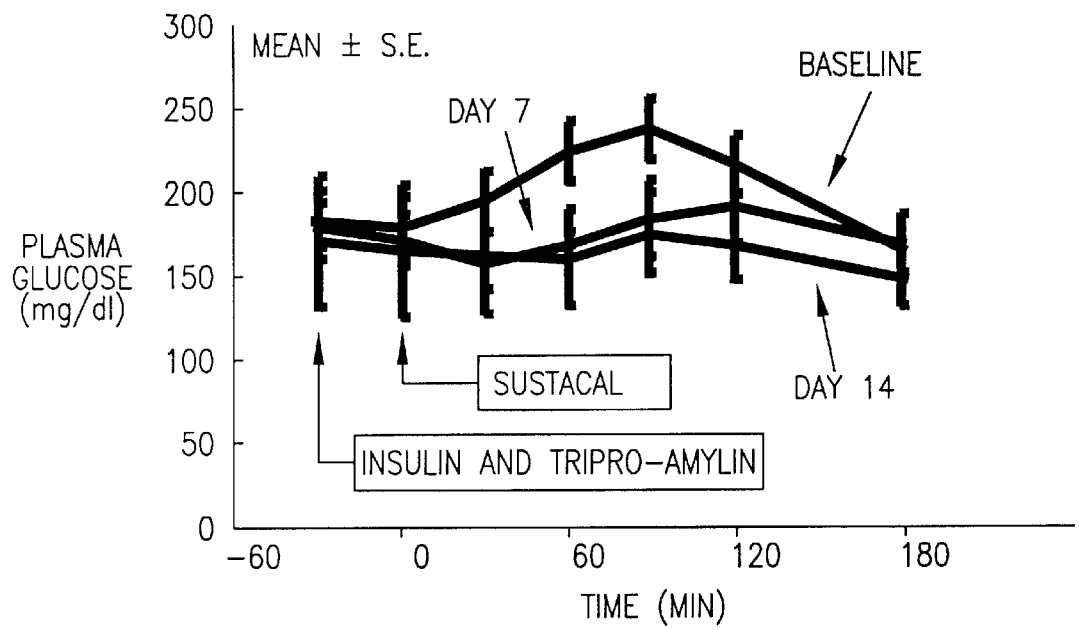
Figure 10A:
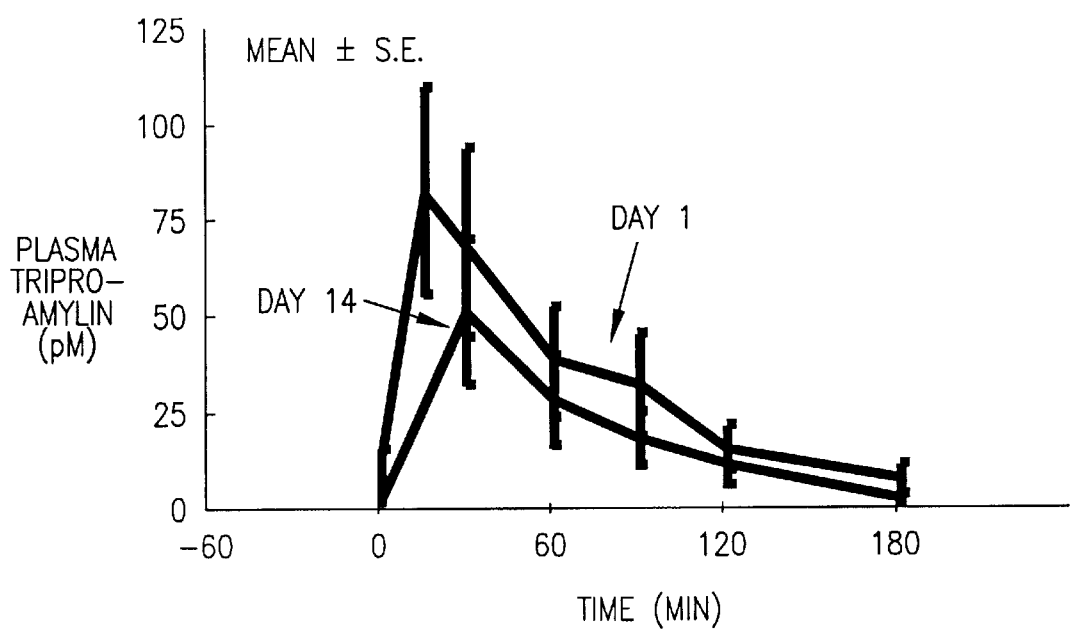

FIG. 10 shows the reduction in post-meal plasma glucose levels, or "glucose smoothing" effect, produced in diabetics administered 100 micrograms of tripro-amylin three times per day over 14 days.

Figure 11:
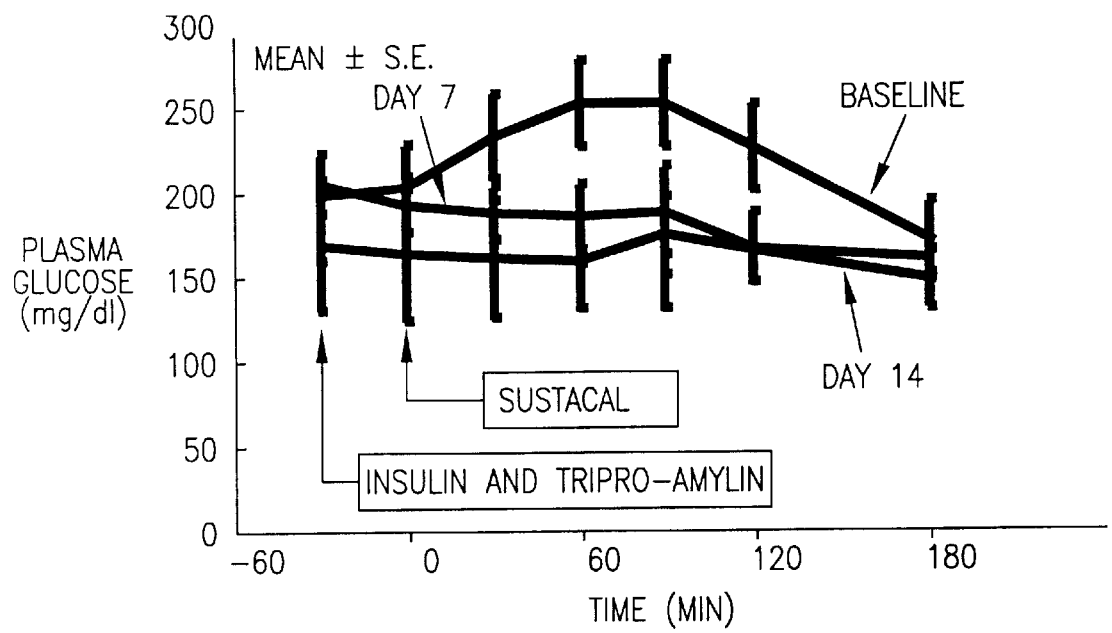
Figure 11A:
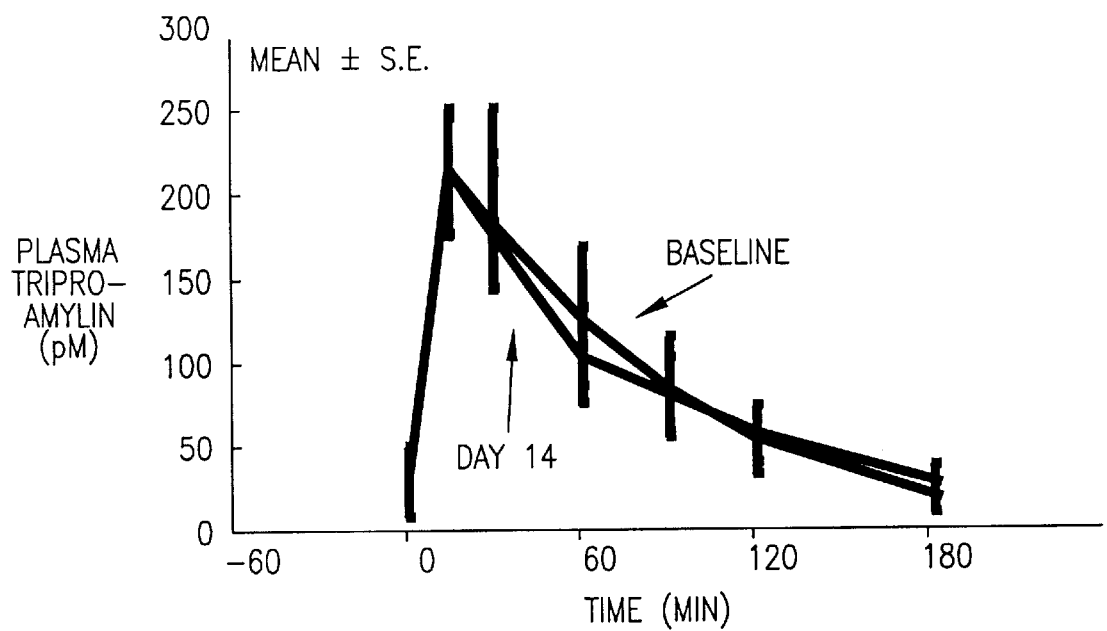

FIG. 11 shows the reduction in post-meal plasma glucose levels, or "glucose smoothing" effect, produced in diabetics administered 300 micrograms of tripro-amylin three times per day over 14 days.

DETAILED DESCRIPTION

The following experiments in Examples 1 and 2 demonstrate the interaction of amylin and insulin in an in vitro and an in vivo test format. These experiments illustrate the surprising nature of interaction of the two hormones in regulation of glycogen metabolism.

As described in more detail below, at low to moderate rates of insulin secretion, the range for most physiologic situations, the response to insulin in the presence of amylin in not much altered. The slope of the insulin dose response is reduced as amylin concentrations begin to reach levels that significantly depress the insulin response. The maximum response achievable is considerably lower than the maximum that could be elicited by insulin alone. As insulin and amylin concentrations rise further, into ranges not normally expected to occur, the insulin response actually declines as increasing amylin action further depresses the functional response to insulin.

Example 3 shows the beneficial effects of administration of representative doses of an amylin (the amylin agonist, "tripro-amylin") to insulin-requiring diabetics in human clinical trials.

EXAMPLE 1

Isolated Soleus Muscle of Rat

Soleus assay, dissection

Male Harlan Sprague Dawley rats of approximately 200 g mass were used in order to maintain soleus muscle mass less than 40 mg. The animals were fasted for 4 hours prior to sacrifice by decapitation. The skin was stripped from the lower limb which was then pinned out on cork board. The tendo achilles was cut just above os calcis and m. gastrocnemius reflected out from the posterior aspect of the tibia. M. soleus, a small 15–205 mm long, 0.55 mm thick flat muscle on the bone surface of m. gastrocnemius was then stripped clear and the perimysium cleaned off using fine scissors and forceps. M. soleus was then split into equal parts using a blade passed antero-posteriorly through the belly of the muscle to obtain a total of 4 muscle strips from each animal. After dissecting the muscle from the animal, it was kept for a short period in physiological saline. The muscle was not held under tension, as reported in other methodologies since in our hands this had no demonstrable effect on the insulin-sensitivity of radioglucose incorporation into glycogen.

Incubation

Muscles were added to 50 mL Erlenmeyer flasks containing 10 mL of a pregassed Krebs-Ringer bicarbonate buffer containing (mM) NaCl 118.5; KCl 5.94; $CaCl_2$ 2.54; $MgSO_4$ 1.19; $KH_2PO_4$ 1.19; $NaHCO_3$ 25; glucose 5.5; and recombinant human insulin (Humulin-R, Eli Lilly, Ind.) and either synthetic rat (Bachem, Torrance, Calif. Lot# ZG485) or synthetic human amylin (Bachem, Torrance, Calif. Lot# ZH144) as detailed below. Methods used to determine the nature and purity of rat and human amylin included quantitative amino acid analysis, gas phase amino acid sequencing, reverse phase HPLC and fast-atom-bombardment mass spectrometry. By the latter two methods, purity was 98.4 and 97.9% respectively. However, application of these methods failed to detect 1 atom of mercury per molecule of rat amylin, which was subsequently detected by electrospray ionization mass spectrometry and atomic absorption spectroscopy. Subsequent analysis of the method of synthesis of the rat amylin suggests that this atom is interposed between the sulfur atoms of cysteine residues 2 and 7, and therefore forms part of the ring structure near the amino-terminus. Incorporation of mercury into rat amylin may be a feature of many commercially available batches that have already been used in published studies. Since the peptide was bioactive, its action in muscle was expected to at least qualitatively mimic that of true rat amylin. The mercuric method of cyclization was not used in the synthesis of human amylin, which is found by electrospray ionization mass spectrometry and atomic absorption spectroscopy to be mercury-free.

Muscles were assigned to different flasks so that the four muscle pieces from each animal were evenly distributed among the different assay conditions. The incubation media were gassed by gently blowing carbogen (95% $O_2$, 5% $CO_2$) over the surface while it was continuously agitated at 37° C. in an oscillating water bath. pH of gassed media at 37° C. was verified as being between 7.1 and 7.4. After a half-hour preincubation, 0.5 $\mu$Ci of [U-$^{14}$C]-glucose was added to each flask for a further 60 minutes. Each muscle piece was then rapidly removed, trimmed of tendons, blotted, frozen in liquid $N_2$, weighed and then stored at 20° C. for subsequent determination of $^{14}$C-glycogen. The incubation medium was also frozen for subsequent analysis. The concentration of human amylin present in the medium at the end of the incubation was determined by radioimmunoassay in surfactant-containing buffer. For both human and rat amylin, the actual mass added to the incubation medium was determined by quantitative amino-acid analysis.

$^{14}$C-Glycoaen Determination

Each frozen muscle specimen was placed in a vial with 1 mL 60% potassium hydroxide (wt/vol) and digested at 70° C. for 45 minutes under intermittent vigorous agitation. Dissolved glycogen was precipitated onto the walls of the vial by addition of 3 mL absolute ethanol and overnight cooling at −20° C. After centrifugation for 30 minutes at 2000 x_g, the supernatant was gently aspirated, the glycogen was again washed with ethanol and centrifuged, the ethanol aspirated and the precipitate dried under vacuum. It was important to evaporate all ethanol to avoid quenching during scintillation counting. The remaining glycogen was redissolved in 1 mL water and 4 mL scintillation fluid and counted for $^{14}$C.

Numerical Methods

A rate of glucose incorporation into glycogen (expressed in $\mu$mol/hr/g wet tissue) was obtained from the specific activity of $^{14}$C-glucose in the 5.5 mM glucose of the incubation medium, and the total $^{14}$C counts remaining in the glycogen extracted from each muscle. Dose response curves were fitted to a 4-parameter logistic model using a least-squares iterative routine (ALLFIT, v2.7, NIH, MD) to derive $EC_{50}$'s. Since $EC_{50}$ is log-normally distributed, it is expressed ± standard error of the logarithm. Pair-wise comparisons were performed using t-test based routines of SYSTAT.

Insulin dose response

Insulin dose response curves were obtained by incubation in media containing insulin added at final concentrations of 0, 0.071, 0.21, 0.71, 2.1, 7.1 and 71 nM[1]/.

[1]/Conversion used, 1$\mu$U/mL=7.1 pM.

Amylin dose response

Amylin dose response curves were generated using muscles added to media containing 7.1 nM recombinant human insulin and either synthetic rat or synthetic human amylin (Bachem, Torrance, Calif.) added at final (nominal) concentrations of 0, 1, 3, 10, 30, 100, 300 and 1000 nM.

A supraphysiological insulin concentration was used for two reasons: (1) the precision of estimation of $EC_{50}$ was related to the magnitude of $^{14}C$ incorporation into glycogen, so greater amylin suppression of the insulin response was possible with near-maximal insulin stimulation; and (2) using an insulin response near the plateau (asymptotic part) of the dose response curve in contrast to the 50% response obtained at the often-used insulin concentration of 710 pM minimized variation in response due to variation in the bathing insulin concentration or individual muscle insulin sensitivities. The effect of using higher insulin concentrations is seen in the reduced standard error of the amylin dose response $ED_{50}$'s detailed in Table 1.

Each assay also contained internal positive controls consisting of a single batch (Bachem Lot# 2G485) of archived rat amylin, lyophilized and stored at −20° C.

Referring to FIG. 9, data pooled from 5 amylin dose response assays performed on a single batch of human amylin in the presence of 7.1 nM insulin are shown. Curve A was fitted to the data obtained when amylin concentration is derived from mass initially weighed out and diluted. Curve B was fitted to data obtained when amylin concentration is derived from mass of peptide added to assay media as determined by quantitative amino-acid analysis. Curve C was fitted to data obtained when amylin concentration in the assay media is measured by radioimmunoassay. The $EC_{50}$ for curve C is 438 pM±0.17 log units (SE).

Insulin/amylin response matrix

The insulin/amylin dose response matrix was obtained by repeating the insulin dose response analyses with amylin added to nominal final concentrations of 0, 3, 10, 30, 100 and 300 nM, thereby generating a 6×6 table with quadruplicates at each combination of insulin and amylin concentrations.

Insulin:amylin fixed ratio dose response

Muscles were incubated in media containing synthetic rat amylin and recombinant human insulin added in a 1:7.1 molar ratio.

Insulin and amylin dose responses

Figure 2:
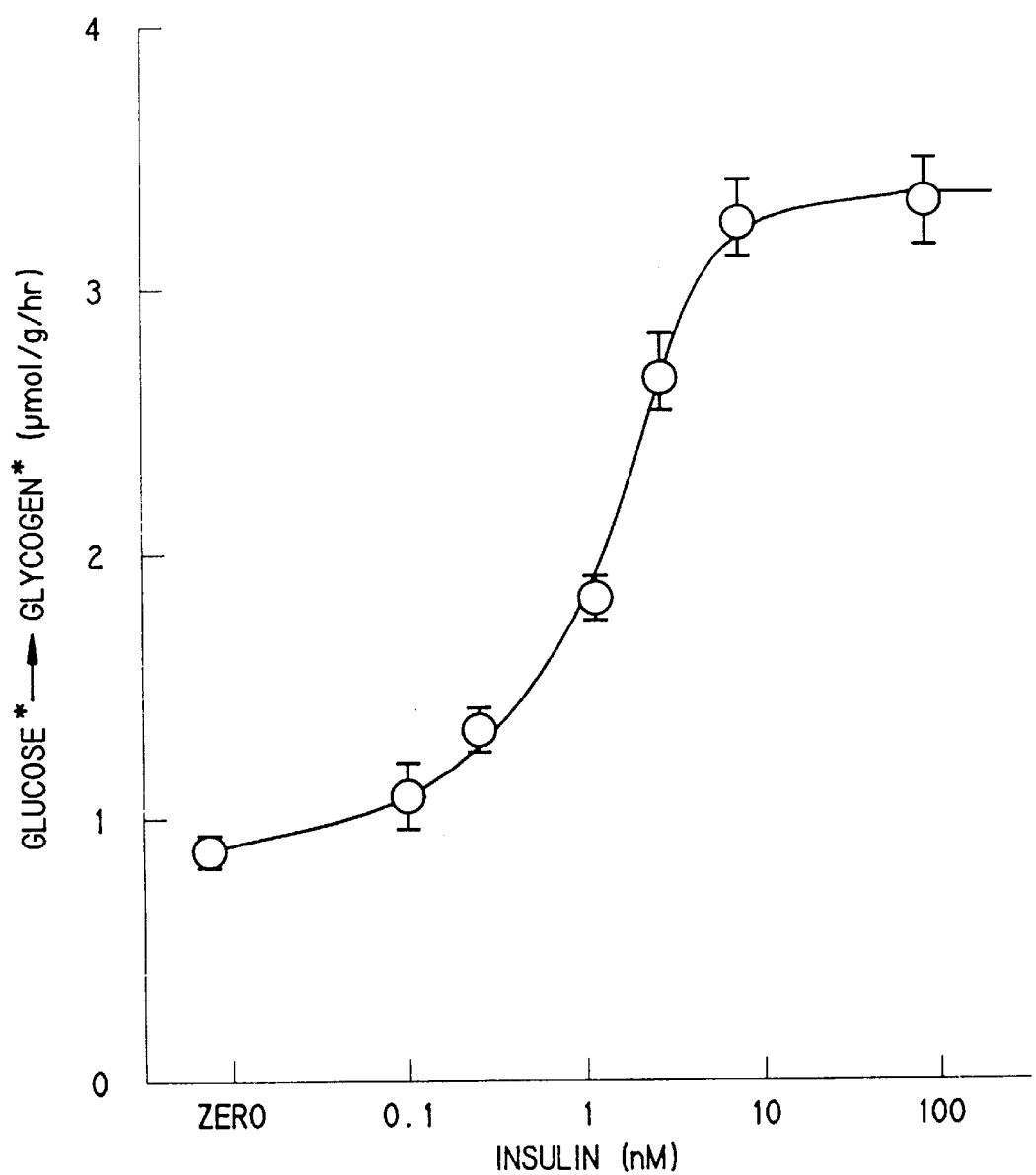
FIG. 2 is a graphical representation of insulin dose response in rat soleus muscle.

Data pooled from 7 insulin dose response assays performed in the absence of amylin are shown in FIG. 2. There was a 3.7-fold increment in rate of glycogen labelling, with an $EC_{50}$ of the response of 1.05 nM±0.07 log units (n=8 to 28 per point).

Combined insulin/amylin dose response

Figure 3:
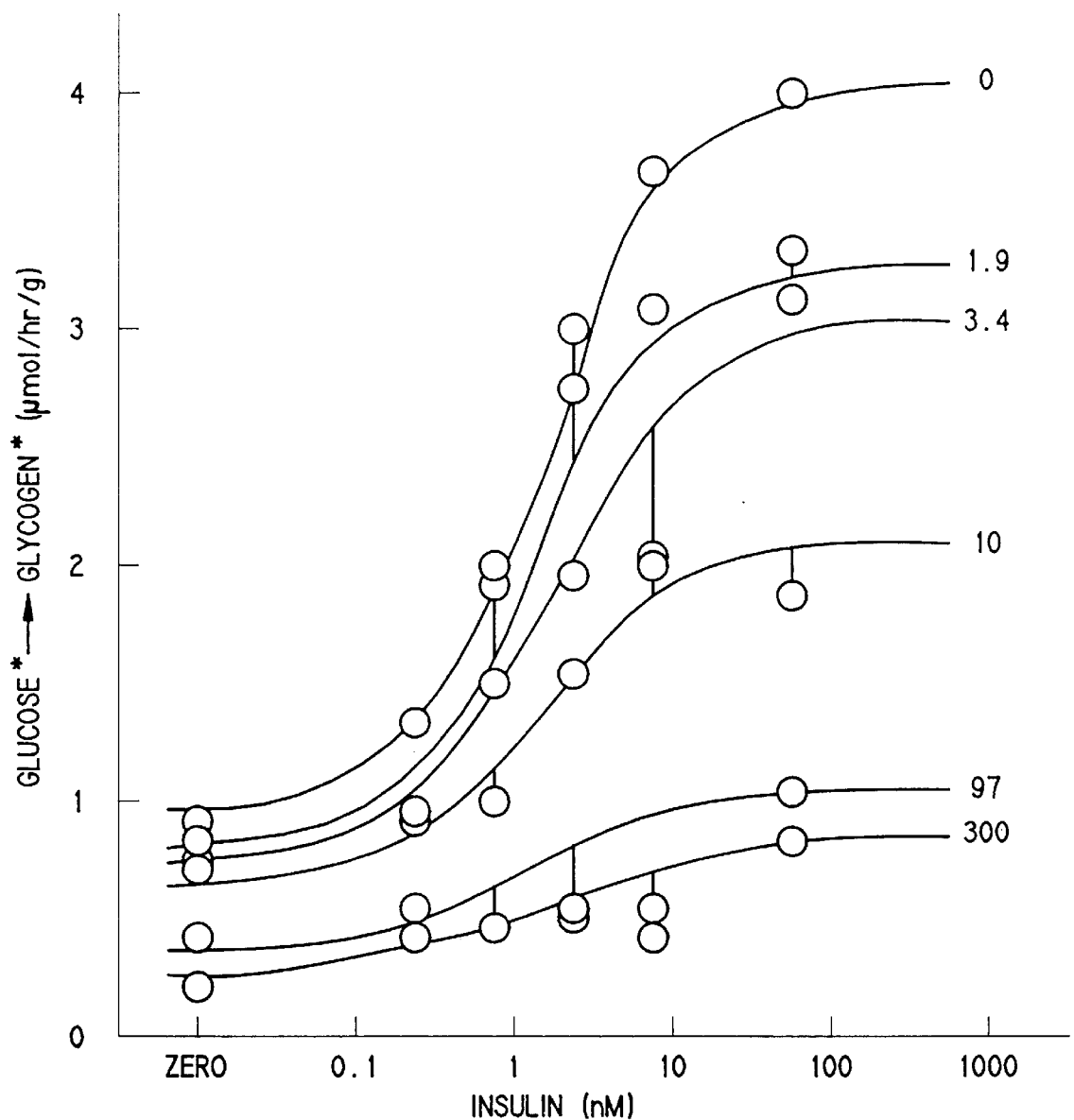
FIG. 3 is a graphical representation of a family of insulin dose response curves with different fixed concentrations of amylin.
Figure 4:
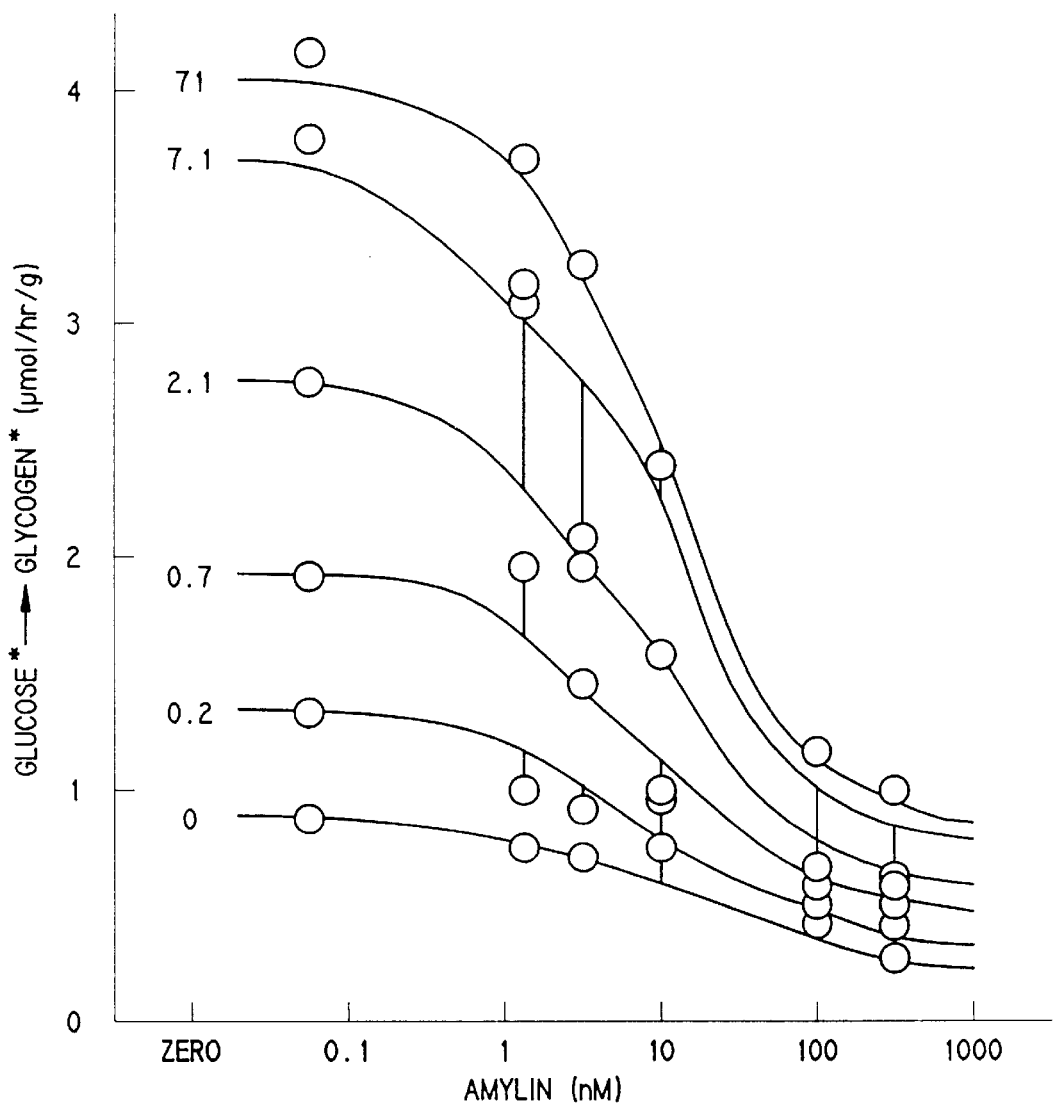
FIG. 4 is a graphical representation of a family of amylin dose response curves with different fixed concentrations of insulin.

FIG. 3 shows a series of insulin dose response curves obtained in the presence of different amylin concentrations as indicated. Data for the maxima and $EC_{50}$'s of the insulin responses are presented in Table 1. They indicate that the $EC_{50}$ of the insulin response was not progressively right-shifted with increasing amylin concentrations. FIG. 4 shows amylin dose response curves obtained with different insulin concentrations, as indicated. Amylin $EC_{50}$'s and maximal responses, presented in Table 1, similarly indicate that the $EC_{50}$ of the amylin response was independent of the prevailing insulin concentration. In other words, amylin could suppress labelling of glycogen at all insulin concentrations. FIG. 5 combines the data from the insulin and amylin dose responses into a single fitted surface. The surface was generated as the product of fractional responses to insulin and amylin, using means of parameters for slope and $EC_{50}$ for the insulin and amylin transects, and plotted on log/log/linear axes.

The equation for the surface is $$\left| \frac{A_{ins} - D_{ins}}{1 + \left(\frac{\text{Insulin}}{C_{ins}}\right) B_{ins}} + D_{ins} \right| \times$$

$$\left| \frac{A_{amy} - D_{amy}}{1 + \left(\frac{\text{Amylin}}{C_{amy}}\right) B_{amy}} + D_{amy} \right| \times F + K$$

The equation thus has the general form . . . Response= [Insulin factor]×[Amylin factor]×F+K where

| | | |
|---|---|---|
| $A_{ins} = 1$ | $A_{amy} = 1$ | (maximal responses) |
| $B_{ins} = -0.889$ | $B_{amy} = 0.835$ | (slope factors) |
| $C_{ins} = 1.42\ nM$ | $C_{amy} = 9.0\ nm$ | ($EC_{50}s$) |
| $D_{ins} = 0.18$ | $D_{amy} = 0.15$ | (basal responses) |
| F (response factor) | | = 4.0 μmol/hr/g wet muscle |
| K (constant) | | = 0.14 |

Insulin and Amylin are concentration in nM

Since the baseplane of the graph is defined by log [insulin] and log [amylin] axes, combinations of insulin and amylin in any given ratio are represented as straight lines on this plane. Lines describing amylin:insulin ratios of 0.01:1, 0.14:1 and 1:1 are projected up onto the surface (labelled 0.01, 0.14 and 1 respectively).

Insulin:amylin fixed ratio dose response

The experimentally determined response to increasing concentrations of a fixed 0.14:1 ratio of amylin:insulin are plotted as open circles in FIG. 6. The bell-shaped function generated from Equation 1, using [amylin]=[insulin]×0.14, and which corresponds to the trajectory labelled "0.14" in FIG. 5, is shown as a continuous line. Also plotted is the sigmoid dose response predicted for insulin in the absence of amylin. The data conform to the bell-shaped profile predicted for non-competitive functional antagonism rather than to a shifted sigmoid response curve as would be predicted for competitive antagonism.

The finding that the $EC_{50}$'s for amylin and insulin action on soleus muscle are not altered by increasing concentrations of the other hormone are consistent with biochemical and pharmacological data indicating that they act via separate receptors rather than by competing at a common receptor. Amylin behaves as a noncompetitive, functional antagonist to insulin. That is, amylin reduces the magnitude of the insulin response without affecting insulin potency. Critically important for analyzing the role of amylin is the finding that it causes insurmountable inhibition of insulin action.

Amylin's biological activity was originally described as an "antagonism" of the muscle response to insulin. Some may therefore have considered that amylin and insulin represent self-canceling signals, and that if these hormones are secreted in a constant ratio, the effects of any increase in plasma amylin would be nullified by the proportionate increase in insulin. The "constant ratio" slices through the response surface (FIG. 4) instead predict that with any fixed ratios of insulin and amylin, suppression by amylin of the insulin response will eventually supervene as the concentrations of both hormones increase. This prediction was confirmed by the experiments shown in FIG. 6. If amylin and insulin were co-secreted in a fixed ratio, the bell-shaped trajectory of FIG. 6 would represent the response of muscle to increasing secretion from the beta-cell. The peak height, the position and shape of the insulin:amylin bell-shaped curve are functions of the muscle sensitivities to insulin and amylin, and their concentration ratio.

TABLE 1

Insuline Dose Response

| [amylin] nM (nominal) | Maximal response µmol/g wet tissue/hr Mean | $EC_{50}$ nm Mean ± log SE |
|---|---|---|
| 0 | 4.09 | 1.16 ± 0.10 |
| 3 | 3.45 | 0.78 ± 0.12 |
| 10 | 3.12 | 1.52 ± 0.15 |
| 30 | 2.13 | 1.33 ± 0.20 |
| 100 | 1.15 | undetermined |
| 300 | 0.93 | undetermined |

Amylin Dose Response

| [insulin] nM (nominal) | Maximal response µmol/g wet tissue/hr Mean ± SEM | $EC_{50}$ nm Mean ± log SE |
|---|---|---|
| 0 | 0.85 ± 0.17 | 12.15 ± 0.94 |
| 0.21 | 1.26 ± 0.18 | 10.27 ± 0.48 |
| 0.71 | 2.11 ± 0.18 | 8.24 ± 0.24 |
| 2.1 | 2.94 ± 0.18 | 10.45 ± 0.16 |
| 7.1 | 3.56 ± 0.19 | 8.69 ± 0.13 |
| 71 | 4.07 ± 0.18 | 11.93 ± 0.11 |

EXAMPLE 2

Daily Amylin replacement reverses hepatic glycogen depletion in insulin-treated streptozotocin diabetic rats.

In streptozotocin-diabetic rats treated with insulin replacement, liver glycogen is some 35% depleted. Five consecutive daily subcutaneous injections with amylin dose-dependently restored liver glycogen to normal levels. Significant increases over insulin-only therapy occurred with amylin doses of 10, 30 and 100 µg/day, representing amylin:insulin ratios of 0.22, 0.75 and 2.79.

Animals

There were 68 male Harlan Sprague Dawley rats (mass 301±3 g) in 8 treatment groups. Animals were housed at 22.7±0.8° C. in a 12:12 hour light:dark cycle (experiments being performed during the light cycle) and fed and watered ad libitum (Diet LM-485, Teklad, Madison, Wis.). The rats were sacrificed for harvesting of livers 4 to 5 hours into the light cycle.

Treatment Groups

1. STZ diabetic, insulin-only treatment (n=11).

Animals were injected with streptozotocin (Sigma Chemical Company, St Louis, Mo.: Sigma 50130) dissolved in water in a dose of 65 mg/kg into the lateral tail vein. Upon exhibiting 5% glycosuria (Chemstrip uGH, Boehringer-Mannheim, FRG), rats were commenced upon a sliding-scale daily insulin treatment regime (Humulin-Ultralente, Eli Lilly, Indianapolis, Ind.) aimed towards maintaining aketonuria (by Chemstrip) but 5% glycosuria. Maintaining diabetic rats in this metabolic state optimizes survival. Following one week of established diabetes, animals received once daily s.c. injections of amylin vehicle (water for injection) for 5 days given at the time of the insulin injection.

2–6 STZ diabetes, insulin+amylin treatment groups.

These animals were treated identically to those in group 1 except that the daily subcutaneous injection contained 3 µg (n=5); 10 µg (n=12); 30 µg (n=5); 100 µg (n=5) or 300 µg (n=5) of rat amylin (Bachem lot# WG485[2]/). The bioactivity of the peptide used in these experiments was first verified by bioassay, using inhibition of insulin-stimulated radioglucose incorporation into glycogen in the isolated stripped rat soleus muscle. The $EC_{50}$ derived for the peptide used was 6.2 nM (±0.2 log unit). The insulin dose in each of the groups of diabetic animals averaged 1.67 U/animal/day. There were no other observable differences in the required management of the different groups.

[2]/This batch of rat amylin has subsequently been found to contain a mercury contaminant, believed to be interposed between the sulphur atoms of the 2-cys 7-cys disulphide bridge.

7. Normal animals (n=10)

These animals were derived from the same stock and housed under the same conditions for the same time as those in groups 1–6, but were given no injections. 24 hours after the fifth daily injection of amylin or water (or an equivalent time after admission to the vivarium in the case of group 7 rats), the non-fasted rats were killed by decapitation and the livers immediately removed and frozen in liquid $N_2$, weighed and stored for subsequent determination of glycogen concentration.

8. STZ-diabetic animals, no treatment (n=10)

These animals were made diabetic as were groups 1–6, but received neither insulin nor amylin.

Glycogen determination

Whole livers were powdered while frozen. Approximately 200 mg of powder was further homogenized in 1.0 mL of 0.6M perchloric acid to denature enzymes. 200 µL of the homogenate was neutralized with 0.5 volumes of 1.0M $KHCO_3$ in either of two acetate buffer solutions, one containing 2.0 mL of 200 mM acetate (pH4.8), the other containing the same but with 18.5 U/mL of amyloglucosidase (EC5 3.2.1.3, from *Aspergillus nicer*, Sigma A3423, Sigma Chemical Company, St Louis, Mo.) added. Following at least 20 minutes incubation at 23° C., the supernatants were assayed for glucose in an analyzer using D-glucose oxidase immobilized enzyme chemistry (Analyzer model 2300-STAT, YSI, Yellow Springs, Ohio). Purified rabbit liver glycogen (Sigma G8876) used as a standard indicated 98±4% recovery of dissolved glycogen and linearity within the range of observed liver glycogen concentrations (r=0.9994). All reagents were of analytical grade or better.

Numerical methods

Statistical comparisons were by Student's t-test routines contained in the SYSTAT system (Systat, Evanston, Ill.). All results are reported as means ± standard error of the mean.

Liver alycogen

Liver glycogen content was measured in rats with free access to food up to the time of sacrifice (fasting rapidly depletes liver glycogen, such that the levels after 18-hours starvation are typically only 2–5% of those observed in the fed state). Glycogen contents for the 8 groups of animals are shown in FIG. 8. STZ diabetic animals on no therapy showed a 67% decrease in liver glycogen concentration compared to normal rats (2.86 vs 8.6 mg/g, P<0.001). STZ diabetic animals receiving insulin replacement had a 35% decrease in liver glycogen compared to normal rats (5.6 vs 8.6 mg/g, P<0.01). In insulin-treated STZ diabetic rats supplemented with daily amylin, there was a dose-dependent increase in liver glycogen concentration above that in rats replaced with insulin alone (P<0.05, 10 µg/day; P<0.02, 30 µg/day; P<0.01, 100 µg/day). The liver glycogen concentration in animals receiving 10, 30 and 100 µg amylin per day was not significantly different from that in normal animals (P<0.3), although the mean values showed a dose-dependent increase with an apparent peak at 30µg/day. The lowest dose examined, 3 µg/day did not measurably increase glycogen levels above those treated with insulin alone. Interestingly, the highest dose of amylin tested, 300 µg/day, also did not measurably restore liver glycogen towards normal, giving an apparently biphasic dose-response.

The results show that combined replacement of amylin and insulin can restore normal levels of liver glycogen in STZ-diabetic rats; full restoration is not achieved with insulin alone. This physiological response is caused by a once-daily subcutaneous injection in a molar ratio of amylin to insulin close to that thought to occur naturally in healthy animals.

EXAMPLE 3
Human Amylin Agonist Clinical Trials

Human clinical trials were conducted with an amylin agonist, [25,28,29]Pro-h-amylin (also referred to as "tripro-amylin" or "AC-0137"). In a total of three studies with more than 100 volunteer patients with juvenile-onset (Type 1) diabetes, the administration of tripro-amylin helped to better control their blood glucose by reducing average blood glucose after a meal. The results were statistically significant and are medically relevant in view of the blood glucose control problems that plague diabetics throughout their lives and, more specifically, for example, because of the abnormally high post-meal glucose levels typical of juvenile-onset diabetes which are understood to be a continuing factor in the onset of long-term medical complications, including blindness, kidney failure, and nerve damage.

In a 14-day double-blind, placebo controlled clinical study, for example, patients with juvenile-onset diabetes who continued their usual insulin therapy and self-injected tripro-amylin three times daily had lower average blood glucose levels after a test meal than did patients who received insulin and placebo. As shown in FIGS. 9–11, after 14 days, a statistically significant (p=0.02) glucose smoothing effect (measured as area under the glucose curve) was observed at the 30, 100, and 300 micrograms/dose level. See also Table 2 below. This effect was, importantly, also observed at 7 days. These thrice-daily doses of tripro-amylin reflect per day dosages of, respectively, 90, 300, and 900 micrograms per patient. For a patient of average weight, about 70 kg, these reflect doses of 1.3 μg/kg/day, 4.3 μg/kg/day, and 12.9 μg/kg/day. An average per day insulin dose is about 50 units, or 2000 micrograms.

TABLE 2

Change in Post Meal Glucose After 14 Days of Tripro-amylin

| Tripro-amylin dose (taken 3 times daily) | placebo | 30 micrograms | 100 micrograms | 300 micrograms |
|---|---|---|---|---|
| Number of patients at 14 days | 21 | 15 | 22 | 12 |
| Post-meal glucose: | | | | |
| Mean of changes in AUC (mg/dl - min.) (a) | +229 | −6,645 | −6,412 | −7,316 |
| "P" values vs. placebo (b) | — | 0.02 | 0.02 | 0.11 |
| Tripro-amylin plasma peaks (picomoles | — | 22 ± 4 | 44 ± 14 | 173 ± 40 |

(a) AUC is area under the glucose concentration curve relative to pre-meal glucose value, between start of test meal and 3 hours later. Change in AUC is value at pre-dosing minus value at day 14 for each subject tested at day 14.
(b) P values obtained from a non-parametric Wilcoxon test.

The effect of tripro-amylin on smoothing post-meal blood glucose levels is an important finding for insulin-requiring diabetics, such as juvenile-onset diabetics (most of whom have difficulty controlling their blood glucose with insulin alone).

The tripro-amylin-induced reductions in AUC accompanied average reductions of 45 mg/dl to 60 mg/dl in the peak blood glucose concentrations of the clinical trial subjects. These results are also important for diabetic subjects, because eating often causes their blood glucose to rise by 60 mg/dl to 160 mg/dl. By contrast, non-diabetic individuals typically show rises of only 30 mg/dl to 45 mg/dl after meals.

The side effect profile for tripro-amylin in the 14-day tests reveals that all measures of safety were satisfactory. The only adverse events which led a limited number of patients to discontinue the study were gastrointestinal side effects, mainly nausea, which were more frequent only in those patients receiving higher doses of drug. About 20% of patients in the mid- and high-dose groups who reported nausea also experienced vomiting on one or more occasions. See Table 3 below.

TABLE 3

Adverse Events

| Tripro-amylin dose (taken 3 times daily) | placebo | 30 micrograms | 100 micrograms | 300 micrograms |
|---|---|---|---|---|
| Patients starting study (a) | 22 | 18 | 23 | 21 |
| Patients reporting any gastrointestinal symptoms | 4 | 5 | 13 | 20 |
| Patients reporting nausea for more than 7 days | 1 | 1 | 8 | 11 |
| Patients who withdrew from the study with nausea | 0 | 1 | 1 | 8 |

TABLE 3-continued

Adverse Events

| Tripro-amylin dose (taken 3 times daily) | placebo | 30 micrograms | 100 micrograms | 300 micrograms |
|---|---|---|---|---|
| Patients reporting other events resulting in early discontinuation | 0 | 0 | 0 | 0 |

(a) In addition to the patients who withdrew from the study due to nausea, four patients who entered the study were not evaluable or did not complete the study for reasons apparently unrelated to study medication.

Following an overnight fast, patients in the 14-day study were challenged with insulin twice: prior to the start of dosing, and after 14 days of placebo or tripro-amylin therapy. The insulin challenge was designed to pharmacologically induce hypoglycemia in a controlled and reproducible manner. In this test, tripro-amylin treatment did not measurably alter the glucose reponse compared to that seen in the placebo group.

Those of ordinary skill in the art reviewing both examples above will recognize that the data indicate to one of ordinary skill in the art that administration of insulin and amylin in the indicated ratios will be an effective treatment for diabetes in humans. Such amylin and insulin can be administered in any standard manner using pharmaceutically acceptable buffers. For example, the hormones may be administered in a form which causes delayed release of the hormones within the body.

Other embodiments are within the following claims.

---

We claim:

1. A method of treating a mammal having a need for, or a reduced ability to produce, insulin, comprising administering to said mammal an insulin having an in vitro activity of stimulating glucose incorporation into glycogen in rat soleus muscle, and an amylin having the in vitro activity of suppressing glucose incorporation into glycogen in rat soleus muscle, wherein said insulin and said amylin are administered in a molar ratio of between about 1:1 and about 67:1.

2. A method according to claim 1 wherein said method further comprises identifying a mammal having a reduced ability to produce serum insulin compared to the normal ability of said mammal to produce serum insulin.

3. A method according to claim 1 wherein said insulin and said amylin are administered in a molar ratio of between about 7:1 and about 67:1.

4. A method according to claim 1 wherein said insulin and said amylin are administered in a molar ratio of between about 1:1 to about 40:1.

5. A method according to claim 4 wherein said insulin and said amylin are administered in a molar ratio of between about 2.5:1 and about 35:1.

6. A method according to claim 4 wherein said insulin and said amylin are administered in a molar ratio of between about 5:1 and about 25:1.

7. A method according to claim 4 wherein said insulin and said amylin are administered in a molar ratio of between about 5:1 and about 10:1.

8. A method according to claim 4 wherein said insulin and said amylin are administered in a molar ratio of between about 4:1 and about 10:1.

9. A method according any of claims 1–8 wherein said amylin comprises $^{25,28,29}$Pro-human amylin.

10. A method according to any of claims 1–5 or 6–8 wherein said amylin comprises $^{25,28,29}$Pro-human amylin and said mammal is a human.

11. A method according to any of claims 1–5 or 6–8 wherein said amylin comprises $^{25,28,29}$Pro-human amylin and said mammal is a human suffering from diabetes mellitus.

12. A method according to claim 1 wherein said amylin is administered in an amount of at least about 0.2 micrograms per kilogram of said mammal per day.

13. A method according to claim 1 wherein said amylin is administered in an amount of at least about 0.4 micrograms per kilogram of said mammal per day.

14. A method according to claim 1 wherein said amylin is administered in an amount of at least about 0.5 micrograms per kilogram of said mammal per day.

15. A method according to claim 1 wherein said amylin is administered in an amount of between about 0.2 micrograms per kilogram of said mammal per day and about 5 micrograms per kilogram of said mammal per day.

16. A method according to claim 15 wherein said amylin is administered in an amount of between about 0.4 micrograms per kilogram of said mammals per day and about 2 micrograms per kilogram of said mammal per day.

17. A method according to any of claims 12–16 wherein said amylin comprises $^{25,28,29}$Pro-human amylin.

18. A method according to any of claims 12–16 wherein said amylin comprises 25,28,29Pro-human amylin and said mammal is a human.

19. A method according to any of claims 12–16 wherein said amylin comprises $^{25,28,29}$Pro-human amylin and said mammal is a human suffering from diabetes.

20. A method according to claim 1 wherein said mammal is a human suffering from diabetes and said amylin is administered in an amount of at least about 90 micrograms per day.

21. A method according to claim 20 wherein said amylin comprises $^{25,28,29}$Pro-human amylin.

22. A method of treating a mammal having a need for, or a reduced ability to produce, insulin, comprising administering to said mammal a composition comprising an insulin having an in vitro activity of stimulating glucose incorporation into glycogen in rat soleus muscle, and an amylin having the in vitro activity of suppressing glucose incorporation into glycogen in rat soleus muscle, wherein said insulin and said amylin are administered in a suitable molar ratio such that, upon administration of such composition to said mammal, the amount of said amylin said composition will result in plasma levels of amylin of about 3% to about 6% the plasma levels of insulin.

23. A method of treating a mammal having a need for, or a reduced ability to produce, insulin, comprising administering to said mammal a composition comprising an insulin having an in vitro activity of stimulating glucose incorporation into glycogen in rat soleus muscle, and an amylin having the in vitro activity of suppressing glucose incorporation into glycogen in rat soleus muscle, wherein said insulin and said amylin are administered in a suitable molar ratio such that, upon administration of such composition to said mammal, the amount of said amylin in said composition will result in plasma levels of amylin of about 4% to about 7% the plasma levels of insulin.

24. A method according to either of claims 22 or 23 wherein said amylin comprises $^{25,28,29}$Pro-human amylin and said mammal is a human.

25. A composition comprising an insulin having an in vitro activity of stimulating glucose incorporation into glycogen in rat soleus muscle, and an amylin having the in vitro activity of suppressing glucose incorporation into glycogen in rat soleus muscle, wherein said insulin and said amylin are provided in a molar ratio of between about 1:1 and about 67:1.

26. A composition according to claim 25 wherein said insulin and said amylin are provided at a molar ratio of between about 7:1 and about 67:1.

27. A composition according to claim 25 wherein said insulin and said amylin are provided at a molar ratio of between about 1:1 to about 40:1.

28. A composition according to claim 27 wherein said insulin and said amylin are provided at a molar ratio of between about 2.5:1 and about 35:1.

29. A composition according to claim 27 wherein said insulin and said amylin are provided at a molar ratio of between about 5:1 and about 25:1.

30. A composition according to claim 27 wherein said insulin and said amylin are provided at a molar ratio of between about 5:1 and about 10:1.

31. A composition according to claim 27 wherein said insulin and said amylin are provided at a molar ratio of between about 4:1 and about 10:1.

32. A composition according to any of claims 25–31 wherein said amylin comprises $^{25,28,29}$Pro-human amylin.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:1:

```
Lys  Cys  Asn  Thr  Ala  Thr  Cys  Ala  Thr  Gln  Arg  Leu  Ala  Asn  Phe  Leu
 1                   5                        10                            15

Val  His  Ser  Ser  Asn  Asn  Phe  Gly  Ala  Ile  Leu  Ser  Ser  Thr  Asn  Val
              20                       25                       30

Gly  Ser  Asn  Thr  Tyr
              35
```

( 2 ) INFORMATION FOR SEQ ID NO:2:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:2:

```
Ala Cys Asp Thr Ala Thr Cys Val Thr His Arg Leu Ala Gly Leu Leu
 1               5                  10                  15
Ser Arg Ser Gly Gly Val Val Lys Asn Asn Arg Val Pro Thr Asn Val
            20                  25                  30
Gly Ser Lys Ala Arg
            35
```

(2) INFORMATION FOR SEQ ID NO:3:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:3:

```
Ala Cys Asn Thr Ala Thr Cys Val Thr His Arg Leu Ala Gly Phe Leu
 1               5                  10                  15
Ser Arg Ser Gly Gly Met Val Lys Ser Asn Arg Val Pro Thr Asn Val
            20                  25                  30
Gly Ser Lys Ala Arg
            35
```

(2) INFORMATION FOR SEQ ID NO:4:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:4:

```
Lys Cys Asn Thr Ala Thr Cys Ala Thr Gln Arg Leu Ala Asn Phe Leu
 1               5                  10                  15
Val His Ser Ser Asn Asn Phe Gly Ala Ile Leu Ser Ser Thr Asn Val
            20                  25                  30
Gly Ser Asn Thr Tyr
            35
```

(2) INFORMATION FOR SEQ ID NO:5:

( i ) SEQUENCE CHARACTERISTICS:
 ( A ) LENGTH: 37 amino acids
 ( B ) TYPE: amino acid
 ( C ) STRANDEDNESS: single
 ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:5:

```
Lys Cys Asn Thr Ala Thr Cys Ala Thr Gln Arg Leu Ala Asn Phe Leu
 1               5                  10                  15
Val His Ser Ser Asn Asn Phe Gly Ala Ile Leu Ser Ser Thr Asn Val
            20                  25                  30
Gly Ser Asn Thr Tyr
            35
```

( 2 ) INFORMATION FOR SEQ ID NO:6:

( i ) SEQUENCE CHARACTERISTICS:
 ( A ) LENGTH: 37 amino acids
 ( B ) TYPE: amino acid
 ( C ) STRANDEDNESS: single
 ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:6:

```
Lys Cys Asn Thr Ala Thr Cys Ala Thr Gln Arg Leu Ala Asn Phe Leu
 1               5                  10                  15
Val Arg Ser Ser Asn Asn Phe Gly Thr Ile Leu Ser Ser Thr Asn Val
            20                  25                  30
Gly Ser Asp Thr Tyr
            35
```

( 2 ) INFORMATION FOR SEQ ID NO:7:

( i ) SEQUENCE CHARACTERISTICS:
 ( A ) LENGTH: 37 amino acids
 ( B ) TYPE: amino acid
 ( C ) STRANDEDNESS: single
 ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:7:

```
Lys Cys Asn Thr Ala Thr Cys Ala Thr Gln Arg Leu Ala Asn Phe Leu
```

```
          1               5                    10                       15
Ile  Arg  Ser  Ser  Asn  Asn  Leu  Gly  Ala  Ile  Leu  Ser  Pro  Thr  Asn  Val
                    20                    25                    30

Gly  Ser  Asn  Thr  Tyr
                    35
```

( 2 ) INFORMATION FOR SEQ ID NO:8:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:8:

```
Lys  Cys  Asn  Thr  Ala  Thr  Cys  Ala  Thr  Gln  Arg  Leu  Ala  Asn  Phe  Leu
 1                    5                    10                       15

Val  Arg  Thr  Ser  Asn  Asn  Leu  Gly  Ala  Ile  Leu  Ser  Pro  Thr  Asn  Val
                    20                    25                    30

Gly  Ser  Asn  Thr  Tyr
                    35
```

( 2 ) INFORMATION FOR SEQ ID NO:9:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:9:

```
Lys  Cys  Asn  Thr  Ala  Thr  Cys  Ala  Thr  Gln  Arg  Leu  Ala  Asn  Phe  Leu
 1                    5                    10                       15

Val  Arg  Ser  Ser  Asn  Asn  Leu  Gly  Pro  Val  Leu  Pro  Pro  Thr  Asn  Val
                    20                    25                    30

Gly  Ser  Asn  Thr  Tyr
                    35
```

( 2 ) INFORMATION FOR SEQ ID NO:10:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:10:

```
Lys  Cys  Asn  Thr  Ala  Thr  Cys  Ala  Thr  Gln  Arg  Leu  Ala  Asn  Phe  Leu
1                   5                        10                            15

Val  Arg  Ser  Ser  Asn  Asn  Leu  Gly  Pro  Val  Leu  Ser  Pro  Thr  Asp  Val
               20                       25                       30

Gly  Ser  Asn  Thr  Tyr
               35
```

( 2 ) INFORMATION FOR SEQ ID NO:11:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:11:

```
Lys  Cys  Asn  Thr  Ala  Thr  Cys  Ala  Thr  Gln  Arg  Leu  Ala  Asn  Phe  Leu
1                   5                        10                            15

Val  His  Ser  Asn  Asn  Asn  Leu  Gly  Pro  Val  Leu  Ser  Pro  Thr  Asp  Val
               20                       25                       30

Gly  Ser  Asn  Thr  Tyr
               35
```

( 2 ) INFORMATION FOR SEQ ID NO:12:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:12:

```
Lys  Cys  Asn  Thr  Ala  Thr  Cys  Ala  Thr  Gln  Arg  Leu  Thr  Asn  Phe  Leu
1                   5                        10                            15

Val  Arg  Ser  Ser  His  Asn  Leu  Gly  Ala  Ala  Leu  Pro  Pro  Thr  Lys  Val
               20                       25                       30

Gly  Ser  Asn  Thr  Tyr
               35
```

( 2 ) INFORMATION FOR SEQ ID NO:13:

(i) SEQUENCE CHARACTERISTICS:
    (A) LENGTH: 37 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:13:

```
Lys Cys Asn Thr Ala Thr Cys Ala Thr Gln Arg Leu Thr Asn Phe Leu
 1               5                  10                  15
Val Arg Ser Ser His Asn Leu Gly Ala Ala Leu Pro Pro Thr Lys Val
            20                  25                  30
Gly Ser Asn Thr Tyr
            35
```